(12) United States Patent
Wagner et al.

(10) Patent No.: US 11,999,678 B2
(45) Date of Patent: Jun. 4, 2024

(54) PROCESS AND PLANT FOR PRODUCING METHANOL

(71) Applicant: L'Air Liquide Société Anonyme pour l'Etude et l'Exploitation des Procédés Georges Claude, Paris (FR)

(72) Inventors: Marc Wagner, Saint Maur des Fosses (FR); Timm Schuhmann, Bensheim (DE); Frank Castillo-Welter, Friedrichsdorf (DE); Tobias Oelmann, Bad Vilbel (DE)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 18/080,394

(22) Filed: Dec. 13, 2022

(65) Prior Publication Data
US 2023/0192576 A1     Jun. 22, 2023

(30) Foreign Application Priority Data
Dec. 20, 2021 (EP) .................................. 21216065

(51) Int. Cl.
C07C 29/152     (2006.01)
B01J 19/00     (2006.01)
B01J 19/24     (2006.01)

(52) U.S. Cl.
CPC ......... *C07C 29/152* (2013.01); *B01J 19/0013* (2013.01); *B01J 19/245* (2013.01); *B01J 2219/0004* (2013.01); *B01J 2219/00051* (2013.01); *B01J 2219/00164* (2013.01)

(58) Field of Classification Search
CPC ...... C07C 31/04; C07C 29/151; C07C 29/152
See application file for complete search history.

(56) References Cited

U.S. PATENT DOCUMENTS

2020/0197890 A1    6/2020    Castillo-Welter et al.
2020/0199054 A1    6/2020    Castillo-Welter et al.

FOREIGN PATENT DOCUMENTS

| EP | 3 401 299 | 11/2018 | |
| EP | 3 401 300 | 11/2018 | |
| EP | 3816145 A1 * | 5/2021 | ............. C01B 3/382 |

OTHER PUBLICATIONS

European Search Report for corresponding EP 21216065, dated May 25, 2022.

* cited by examiner

*Primary Examiner* — Jafar F Parsa
(74) *Attorney, Agent, or Firm* — Elwood L. Haynes

(57) ABSTRACT

The invention relates to a process and a plant for producing methanol in which a compressed make-up gas stream which contains at least one carbon oxide and hydrogen is combined with a residual gas to afford a synthesis gas stream and reacted to afford methanol. According to the invention the residual gas stream and the make-up gas stream are combined using a jet pump, wherein the compressed make-up gas stream is supplied to the jet pump as motive medium via its motive media connection at a pressure $p_1$ and the residual gas stream is supplied to the jet pump as suction medium via its suction port at a pressure $p_3$ and wherein the synthesis gas stream is discharged from the jet pump via its pressure port at a pressure $p_2$ and subsequently supplied to the synthesis stage and wherein $p_1 > p_2 > p_3$.

5 Claims, 2 Drawing Sheets

PROCESS AND PLANT FOR PRODUCING METHANOL

CROSS REFERENCE TO RELATED APPLICATIONS

This application claims the benefit of priority under 35 U.S.C. § 119 (a) and (b) to European Patent Application No. 21216065.9, filed Dec. 20, 2021, the entire contents of which are incorporated herein by reference.

FIELD OF THE INVENTION

The present invention relates to a process and plant for producing methanol on an industrial scale using a jet pump as a means for recycling the synthesis gas not converted in the methanol synthesis.

BACKGROUND

On a large industrial scale methanol is produced from synthesis gas. Synthesis gas is a mixture of predominantly hydrogen ($H_2$), carbon monoxide (CO) and carbon dioxide ($CO_2$). It further comprises smaller amounts of gas constituents inert under the conditions of methanol synthesis. Carbon monoxide and carbon dioxide are often subsumed in the term "carbon oxides". In the process today described as low-pressure methanol synthesis the synthesis gas is converted into methanol and water (as a necessarily generated by-product) at a synthesis pressure of 60 to 120 bar. After compression to the respective synthesis pressure the employed synthesis gas, often referred to as make-up gas, is passed through a catalyst bed of a methanol synthesis catalyst at catalyst temperatures of typically more than 200° C. The methanol synthesis catalyst is typically a composition comprising copper as the catalytically active species. Depending on the process mode one or more serially arranged or parallel synthesis stages (reactor stages), each having an appropriate catalyst bed, are employed. The conversion of the carbon oxides into methanol and water over the catalyst is incomplete on account of the establishment of a thermodynamic equilibrium according to the reactions $$CO_2 + 3H_2 \rightleftharpoons CH_3OH + H_2O,$$

$$CO + 2H_2 \rightleftharpoons CH_3OH$$

As a result the production process is typically run as a recirculating process in a so-called loop. The reaction mixture obtained at the outlet from the respective synthesis stage is cooled to below the boiling point of methanol to discharge from the circuit a mixture of methanol and water (and also undesired condensable byproducts) referred to as raw methanol. At the same time unconverted synthesis gas is recycled to the methanol synthesis catalyst for re-reaction after combination with the make-up gas. The unconverted synthesis gas, also known as residual gas or recycle gas, has a substream withdrawn from it continuously as a purge stream to avoid the concentration of inert constituents in the synthesis loop increasing over time.

The makeup gas is typically produced at pressures between 20 and 40 bar and compressed to a higher pressure level of typically markedly above 60 bar via a so-called synthesis gas or makeup gas compressor for the methanol synthesis. The process operates with relatively high gas recirculation rates through the reactor part in order to achieve a sufficient conversion according to the yield of carbon and hydrogen converted into methanol. The compression work for the residual gas is generally performed with an additional compression stage of the make-up gas compressor (in particular at high capacities) or with an additional machine, i.e. a dedicated residual gas compressor (especially in the case of small capacities). Depending on the reactor system and the composition of the make-up gas the recycled volume flow of residual gas is up to 5 times higher than the volume flow of make-up gas from synthesis gas production. This is especially the case for synthesis gas having a high carbon dioxide content where the thermodynamic equilibrium conversion is low. The quotient of residual gas volume flow and make-up gas volume flow is also known as the recirculation rate.

Addition of further synthesis stages including intermediate condensation of the obtained raw methanol makes it possible to increase the conversion "per pass". This allows the recirculation rate to be reduced. This principle is described for example in EP 3 401 299 A1 and EP 3 401 300 A1.

SUMMARY

The additional compressor or the additional compressor stage for compressing and recycling the residual gas to the reactor inlet is a costly apparatus which entails high maintenance requirements and is prone to malfunctions. The apparatus arranged in the vicinity of the reactor further requires additional area and structural steel for installation and operation. Such an apparatus further requires appropriate instrumentation for operation and control, Lubrication and sealing of the apparatus in the context of regular maintenance is also time- and cost-intensive.

It is an object of the present invention to provide a process and a plant for producing methanol which at least partially overcomes the disadvantages of the prior art.

It is in particular an object of the present invention to provide a process which makes it possible to replace the residual gas compressor or the additional compressor stage by a less costly component which is easier to maintain.

It is a further object of the present invention to provide a process which makes it possible to replace the residual gas compressor or the additional compressor stage by a less costly component which is easier to maintain for small- and intermediate-scale plants.

It is a further object of the present invention to provide a process which makes it possible to replace the residual gas compressor or the additional compressor stage by a less costly component which is easier to maintain for plants which utilize the principle of multistage synthesis of methanol with intermediate condensation.

It is a further object of the present invention to provide a process which makes it possible to replace the residual gas compressor or the additional compressor stage by a less costly component which is easier to maintain for processes which utilize a synthesis gas having a high carbon monoxide content.

It is a further object of the present invention to provide a process which makes it possible to replace the residual gas compressor or the additional compressor stage by a less costly component which is easier to maintain for processes which utilize a synthesis gas having a high carbon dioxide content and the principle of multistage synthesis of methanol with intermediate condensation.

It is a further object of the present invention to propose a plant which at least partially achieves at least one of the abovementioned objects.

The independent claims make a contribution to the at least partial achievement of at least one of the above objects. The dependent claims provide preferred embodiments which contribute to the at least partial achievement of at least one of the objects. Preferred embodiments of constituents of one category according to the invention are, where relevant, likewise preferred for identically named or corresponding constituents of a respective other category according to the invention.

The terms "having", "comprising" or "containing", etc., do not preclude the possible presence of further elements, ingredients, etc. The indefinite article "a" does not preclude the possible presence of a plurality.

The abovementioned objects are at least partially achieved by a process for producing methanol, wherein the process comprises the steps of:
 a) providing and compressing a make-up gas stream MG, wherein the make-up gas stream MG comprises at least one carbon oxide and hydrogen;
 b) reacting a synthesis gas stream SG in a synthesis stage over a solid methanol synthesis catalyst, wherein raw methanol and a residual gas stream RG are obtained and wherein the raw methanol after cooling and condensation as liquid reaction product and the residual gas stream RG are discharged from the synthesis stage;
 c) combining the residual gas stream RG with the make-up gas stream MG to obtain the synthesis gas stream SG, characterized in that the residual gas stream RG and the make-up gas stream MG are combined using a jet pump, wherein the compressed make-up gas stream MG is supplied to the jet pump as motive medium via its motive media connection at a pressure $p_1$ and the residual gas stream RG is supplied to the jet pump as suction medium via its suction port at a pressure $p_3$ and wherein the synthesis gas stream SG is discharged from the jet pump via its pressure port at a pressure $p_2$ and subsequently supplied to the synthesis stage and wherein $p_1 > p_2 > p_3$.

According to the invention the residual gas compressor or the additional compressor stage are replaced by a jet pump. Jet pumps are apparatuses known to those skilled in the art for conveying, compressing or mixing of gases, liquids or solids. They are pumps without movable parts which perform work by converting pressure energy into velocity. The basic principle is that a liquid or gaseous jet exits a nozzle at high velocity and entrains and accelerates a liquid, a gas or a solid from its environment. This results in a mixture of motive and entrained (aspirated) matter whose velocity is reduced again in a second nozzle by pressure elevation.

A jet pump, in particular the jet pump according to the invention, may also be referred to as an ejector. According to the invention the jet pump or the injector is in particular a so-called gas jet pump since exclusively gaseous substances are conveyed. Such a gas jet pump may also be referred to as a gas jet compressor.

The jet pump according to the present invention comprises a motive media connection, a suction port and a pressure port. The compressed make-up gas stream MG serves as motive medium and is therefore applied to the jet pump via its motive media connection. A motive nozzle is usually arranged downstream of the motive media connection of the jet pump. The motive nozzle accelerates the motive medium, here the compressed make-up gas stream MG, to produce a low-pressure region. This causes the suction medium aspirated via the suction port, here the residual gas stream RG, to be entrained. The entrained section medium is compressed by the motive medium. The motive medium and the suction medium are typically mixed inside the mixing chamber of the jet pump arranged in the head region of the jet pump. The resulting mixture of motive and entrained gas, here the synthesis gas SG, subsequently exits the jet pump via the pressure port, A diffuser is especially arranged between the mixing chamber and the pressure port. Inside the diffuser the velocity decreases and the pressure is restored. The flow channel of the diffuser especially consists of a portion narrowing in the flow direction, the inlet cone, a cylindrical part, the mixing nozzle and a widening portion, the outlet cone. Decisive for the functioning of the jet pump are the pressures and associated mass flows prevailing at its connections.

The compressed make-up gas stream MG is supplied to the jet pump via its motive medium connection at a pressure $p_1$. The pressure $p_1$ is thus the so-called motive media pressure upstream of or at the motive media connection. The residual gas stream RG is supplied to the jet pump via its suction port at a pressure $p_3$. The pressure $p_3$ is thus the so-called suction pressure upstream of or at the suction port. The synthesis gas stream SG is discharged from the jet pump via its pressure port at a pressure $p_2$. The pressure $p_2$ is thus the so-called counterpressure downstream of or at the pressure port. Here, $p_1 > p_2 > p_3$, i.e. the motive media pressure is highest, the suction pressure is lowest and the counterpressure is between the motive media pressure and the suction pressure.

Since the counterpressure $p_2$ at the pressure port of the jet pump is higher than the suction pressure $p_3$ the residual gas stream RG is effectively compressed by means of the compressed make-up gas stream MG.

In context of the process according to the invention this means that only one make-up gas compressor for compressing the provided make-up gas stream is required. The compressed make-up gas stream MG has a pressure of at least $p_1$ after compression. The pressure $p_3$ is at least equal to the synthesis pressure at which the synthesis gas stream SG is supplied to the synthesis stage. A dedicated residual gas compressor (recycle gas compressor) or an additional compressor stage at the make-up gas compressor is thus not required in the process according to the invention. In one embodiment the process according to the invention thus does not include a step for compressing the residual gas stream RG in a (dedicated) residual gas compressor stage. In a further embodiment the process according to the invention includes only a single compression stage of a make-up gas compressor for compressing the make-up gas stream MG.

The use of a jet pump has the advantage that jet pumps have no moving or movable parts, in particular have no rotating parts in contrast to the typically employed compressors. They are therefore low-maintenance. Furthermore, jet pumps do not require a separate energy source, for example electrical energy or heat energy. On the contrary jet pumps operate on the basis of the principle of converting pressure energy into kinetic energy and vice versa.

Although the power demand for compression of the make-up gas stream MG via the make-up gas compressor increase when using a jet pump for compressing the residual gas stream MG (higher operating costs) this disadvantage is overcompensated by the use of a jet pump for compressing the residual gas stream RG in the sense that an additional residual gas compressor or an additional compressor stage for the make-up gas compressor can be avoided (lower capital and maintenance costs). This applies especially to processes and plants having relatively small and intermediate capacities and thus a lower methanol production per unit time than large-scale plants. In relatively small and intermediate-scale plants it is especially advantageous when, due to lower expected volumes relative to large-scale plants, capital and maintenance costs can be reduced.

The make-up gas stream MG especially comprises carbon oxide and hydrogen. The term "carbon oxide" is to be understood as meaning either carbon monoxide or carbon dioxide. The make-up gas stream MG thus comprises at least carbon monoxide and hydrogen or
carbon dioxide and hydrogen or
carbon monoxide, carbon dioxide and hydrogen.

The make-up gas stream optionally further comprises undesired constituents, in particular constituents inert under the conditions of methanol synthesis such as methane and/or nitrogen. The make-up gas stream MG is in particular provided via a process known to those skilled in the art for producing synthesis gas from a fossil carbon source, for example steam reforming (SMR), autothermal reforming (ATR), partial oxidation (Pox), coal gasification or combinations therewith or therefrom. The synthesis gas stream may further at least partially derive from a non-fossil carbon source. Thus, synthesis gas may be produced for example through gasification of biomass or communal wastes. The "production" of synthesis gas by combination of "green" hydrogen, for example from the electrolysis of water and carbon dioxide from an incineration plant, for example a refuse incineration plant, is also conceivable.

The conversion of the synthesis gas SG to raw methanol is carried out over the methanol synthesis catalyst. The term "raw methanol" is to be understood as meaning a mixture of methanol and water which may further comprise non-condensable and condensable undesired byproducts. The reaction is carried out in a synthesis loop, i.e. synthesis gas from the synthesis gas stream SG not converted over the catalyst is recycled to the residual gas stream RG and mixed with fresh synthesis gas (make-up gas) from the make-up gas stream MG) using the jet pump. The conversion of the synthesis gas stream SG over the methanol synthesis catalyst is preferably carried out at a catalyst temperature of 220° C. to 270° C. and preferably a pressure of 55 bar to 80 bar. Before compression by a make-up gas compressor the make-up gas has a pressure of 20 bar to 40 bar for example.

Separation of the raw methanol from the residual gas stream RG is effected by cooling the product gas mixture comprising raw methanol and residual gas preferably below the dew point of methanol. As a result the raw methanol condenses and may therefore be separated from the still gaseous residual gas stream RG. Raw methanol is thus discharged from the synthesis stage as liquid reaction product after cooling and condensation (and separation of gaseous residual gas stream RG). The residual gas stream RG is likewise discharged from the synthesis stage as a gaseous stream separated from the liquid reaction product.

A preferred embodiment of the process according to the invention is characterized in that for a recirculation rate R defined as $$R = \frac{\text{Volume flow}(RG)}{\text{Volume flow}(MG)},$$

$0.3 \leq R \leq 2.0$, preferably $0.5 \leq R \leq 1.5$, more preferably $1.0 \leq R \leq 1.5$.

The recirculation rate R is defined as the quotient of the volume flow of the residual gas stream RG and the volume flow of the make-up gas stream MG. The recirculation rate R thus determines how much residual gas not converted in the synthesis stage and how much compressed make-up gas is present in the synthesis gas stream SG.

A recirculation rate R of 0.3 to 2.0, preferably 0.5 to 1.5, more preferably 1.0 to 1.5, is relatively low and may be realized in particular when the thermodynamic equilibrium of the reaction of the synthesis gas mixture to afford raw methanol is shifted relatively markedly towards the product side. In this case only a relatively small portion of the residual gas stream RG must be recycled to the synthesis stage. The power demand of the compression work is in this case determined mainly via the compression of the make-up gas stream to afford make-up gas stream MG and to a lesser extent via compression of the residual gas stream RG. It is therefore possible, especially at relatively low recirculation rates R such as those mentioned above, to avoid a dedicated residual gas compressor and instead to realize the compression work for the residual gas stream RG by means of a jet pump as described above.

Low recirculation rates such as those mentioned above are in particular also realizable in the case of single-stage methanol syntheses in the case where the proportion of carbon monoxide in the carbon oxide mixture is particularly high, so that the reaction equilibrium is markedly on the product side. This is the case for synthesis gas from coal gasification for example. In a corresponding embodiment the proportion of carbon monoxide in the carbon oxides in the make-up gas stream MG is at least 50% by volume or at least 75% by volume or at least 90% by volume.

A preferred embodiment of the process according to the invention is characterized in that the process comprises a plurality N of serially arranged synthesis stages wherein the raw methanol after cooling and condensation as liquid reaction product is discharged from each of the synthesis stages and the residual gas stream RG is discharged from the last of the N synthesis stages.

In this preferred embodiment the process comprises a plurality of synthesis stages, i.e. at least two synthesis stages. These synthesis stages are arranged in series and each of the synthesis stages comprises an intermediate condensation for discharging raw methanol from the respective synthesis stage. In other words each of the N synthesis stages is followed by a cooling and condensation for discharging the raw methanol from the respective synthesis stage. The simultaneously produced stream of unconverted synthesis gas per synthesis stage is transferred into the respective downstream synthesis stage provided it is not the last of the N synthesis stages that is concerned. The gas stream transferred into the respective downstream synthesis stage is in the context of the present invention referred to as an intermediate gas stream IG. Thus for example the unconverted synthesis gas from the first synthesis stage of a process having three synthesis stages is transferred into the second synthesis stage as first intermediate gas stream IG 1 and further converted therein. The unconverted synthesis gas from the second synthesis stage of the process is transferred into the third synthesis stage as second intermediate gas stream IG 2 and further converted therein.

Thus, in general terms, if the process has N synthesis stages the process accordingly has N−1 intermediate gas streams IG. The intermediate gas stream of an nth synthesis stage of the N synthesis stages is thus transferred into the respective (n+1)th synthesis stage and further converted therein unless the nth synthesis stage is the last of the serially arranged N synthesis stages.

Unconverted synthesis gas from the third or, in general terms, last of the N synthesis stages corresponds to the residual gas stream RG that is combined with the make-up gas MG using the jet pump. It is further also possible for a portion of the intermediate gas stream IG or a portion of two or more of the intermediate gas streams IG to be combined with the make-up gas stream MG.

In a multistage synthesis defined according to this embodiment the carbon conversion "per pass" is always higher than in a single-stage synthesis. Accordingly, the volume flow of the residual gas stream RG is lower. This applies correspondingly to the recirculation rate R which for an identical starting material (composition of the make-up gas stream MG) is always lower than for a single-stage synthesis. Accordingly, the abovementioned advantages of the use of a jet pump for compressing the residual gas stream RG at lower recirculation rates come into effect in particular in a multistage synthesis since a low recirculation rate R is intrinsic to a multistage synthesis.

A preferred embodiment of the process according to the invention is characterized in that for the plurality N of serially arranged synthesis stages N≥2, preferably 2≤N≤5, more preferably 3≤N≤4.

It is thus preferable when the process according to the invention comprises 2 to 5 serially arranged synthesis stages and preferably 3 or 4 synthesis stages. Additional synthesis stages with integrated product separation, i.e. intermediate condensation of the product mixture and separation thereof, reduce the required volume flow of residual gas (residual gas stream RG) at unchanged overall production relative to a single-stage process as a reference. This is advantageous having regard to the use according to the invention of a jet pump since, as described above, the compression work for the residual gas stream RG may primarily be realized using the jet pump. However, with an increasing number of synthesis stages the total pressure drop in the synthesis loop increases, which in turn entails additional compression work having regard to the residual gas stream RG and depending on further boundary parameters of the system the use of a jet pump may then in some cases no longer be advantageous. The use of an intermediate number of synthesis stages, in particular 2 to 5 synthesis stages and preferably 3 or 4 synthesis stages, is therefore advantageous in this respect. This is especially advantageous when this number of synthesis stages is combined with the abovementioned low recirculation rates R of 0.3≤R≤2.0, preferably 0.5≤R≤1.5, more preferably 1.0≤R≤1.5.

A preferred embodiment of the process according to the invention is characterized in that the proportion of carbon dioxide in the carbon oxides in the make-up gas stream MG is at least 50% by volume or at least 75% by volume or at least 90% by volume.

Carbon dioxide-rich synthesis gas is in particular used in multistage methanol syntheses since the thermodynamic equilibrium of the methanol forming reaction is in this case markedly on the reactant side. In order nevertheless to generate a high carbon conversion a multistage synthesis having two or more stages and intermediate condensation per stage is thus often used in this case. Such a recirculation rate R as defined above can also be realized when using carbon dioxide-rich synthesis gases or even carbon monoxide-free synthesis gases. The use of a jet pump according to the invention has specific advantages at low recirculation rates R as described above.

The abovementioned objects are further at least partially achieved by a plant for producing methanol, wherein the plant comprises the following components in operative connection with one another:

a) a compressor for compressing a make-up gas stream MG, wherein the make-up gas stream MG comprises at least one carbon oxide and hydrogen;
b) a reaction apparatus for reacting a synthesis gas stream SG in a reactor stage over a solid methanol synthesis catalyst, wherein raw methanol and a residual gas stream RG are obtainable by the reaction over the methanol synthesis catalyst and wherein the reactor stage comprises means for cooling and condensing the raw methanol and means for discharging the raw methanol as liquid reaction product and the residual gas stream from the reactor stage;
c) means for combining the residual gas stream RG and the make-up gas stream MG by which the synthesis gas stream SG is obtainable, characterized in that the plant comprises a jet pump as a means for combining the residual gas stream RG and the make-up gas stream MG and the plant comprises means for supplying the compressed make-up gas stream MG to a motive media connection of the jet pump at a pressure $p_1$, thus making the make-up gas stream MG employable as the motive medium of the jet pump, and the plant comprises means for supplying the residual gas stream RG to a suction media connection of the jet pump at a pressure $p_3$ and the synthesis gas stream SG is dischargeable from the jet pump and suppliable to the reaction apparatus via a pressure port of the jet pump at a pressure $p_2$ and wherein $p_1 > p_2 > p_3$.

Having regard to the plant according to the invention, which is also suitable for performing the process according to the invention, the term "synthesis stage" used for the process according to the invention is substituted by the term "reactor stage". The reaction apparatus used for reacting the synthesis gas stream SG to afford raw methanol may also be referred to as a reactor and comprise two or more such reactor stages.

A preferred embodiment of the plant according to the invention is characterized in that the reaction apparatus of the plant comprises a plurality P of serially arranged reactor stages wherein the raw methanol after cooling and condensation as liquid reaction product is dischargeable from each of the reactor stages and the residual gas stream RG is dischargeable from the last of the P reactor stages.

The plurality P of serially arranged reactor stages corresponds to the plurality N of serially arranged synthesis stages of the process according to the invention.

A preferred embodiment of the plant according to the invention is characterized in that for the plurality P of reactor stages P≥2, preferably 2≤P≤5, more preferably 3≤P≤4.

The plant according to the invention is in particular configured such that the plant is operable at a recirculation rate R defined as $$R = \frac{\text{Volume flow}(RG)}{\text{Volume flow}(MG)},$$

and 0.3≤R≤2.0, preferably 0.5≤R≤1.5, more preferably 1.0≤R≤1.5.

BRIEF DESCRIPTION OF THE DRAWINGS

The invention is more particularly elucidated hereinbelow by way of two inventive examples without in any way limiting the subject-matter of the invention.

Further features, advantages and possible applications of the invention will be apparent from the following description of the exemplary embodiments in connection with the drawings.

DESCRIPTION OF THE PREFERRED EMBODIMENTS

Figure 1:
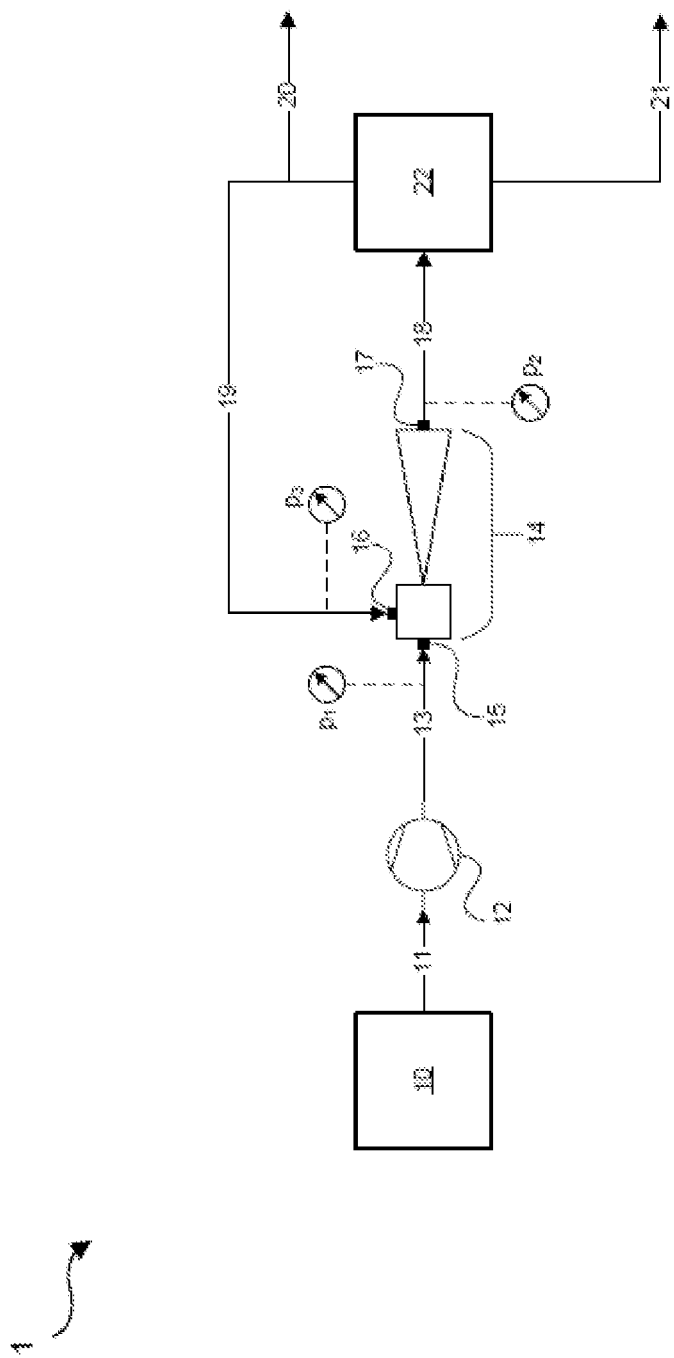
FIG. 1 shows a block flow diagram of an inventive process or an inventive plant according to a first example of the invention, wherein the process comprises a single synthesis stage.

FIG. 1 shows a highly simplified block flow diagram of an inventive process (or an inventive plant) 1 according to a first example of the invention. The process according to FIG. 1 comprises only a single synthesis stage (or reactor stage) 22. The process comprises an apparatus for synthesis gas production 10, for example a steam reformer. The apparatus 10 produces a synthesis gas which comprises at least carbon monoxide, carbon dioxide and hydrogen and as make-up gas stream 11 at a pressure of 30 bar is compressed in compressor 12 to 95 bar. The compressed make-up gas stream MG 13 is subsequently supplied to an inventive jet pump 14 via its motive media connection 15. The jet pump 14 further comprises a suction port 16 and a pressure port 17. After entry of the compressed make-up gas stream MG 13 via the motive media connection 15 of the jet pump 14 said stream is accelerated by a motive nozzle (not shown) present in the jet pump 14, as a result of which a region of relatively low pressure is generated in the head region of the jet pump 14 and a residual gas stream 19 supplied via the suction port 16 is thus entrained. Mixing of the streams 13 and 19 inside the jet pump 14 thus produces a synthesis gas stream 18 which exits the jet pump 14 at the pressure port 17. The synthesis gas stream 18 has a pressure which is lower than the pressure of the compressed make-up gas stream MG 13 and higher than the pressure of the residual gas stream RG 19. In any case the synthesis gas stream SG 18 has a pressure which is at least as high as the synthesis pressure required for the methanol synthesis which is necessary for the conversion of the synthesis gas into methanol in the synthesis stage 22.

The process further comprises three measurement and control sites for detecting and adjusting the pressures of the streams 13, 19 and 18 which are supplied to the jet pump 14 or discharged therefrom. Any required control valves or other measurement and control means are not shown. The pressure $p_1$ is the motive media pressure, i.e. the pressure of the compressed make-up gas stream MG 13 upstream of the motive media connection 15 of the jet pump 14. The pressure $p_3$ is the suction pressure, i.e. the pressure of the residual gas stream RG 19 upstream of the suction port 16 of the jet pump 14. Finally, the pressure $p_2$ is the counterpressure, i.e. the pressure of the synthesis gas stream 18 immediately downstream of the outlet, i.e. pressure port 18, of the jet pump 14.

The synthesis gas stream SG 18 exiting via the pressure port 17 of the jet pump 14 is supplied to the synthesis stage (or reactor stage) 22 and therein converted into raw methanol, a mixture of methanol and water and any undesired byproducts, over a solid methanol synthesis catalyst. The synthesis stage 22 comprises means for discharging the reaction heat of the exothermic methanol formation reaction and for cooling and condensing the raw methanol which is subsequently separated from the residual gas stream RG 19 as raw methanol stream 21 by a separation step and discharged from the synthesis stage 22 as liquid reaction product. The residual gas stream RG 19 from the synthesis stage 22 is also discharged and recycled to the suction port of the jet pump 14 and thus combined with the make-up gas stream MG 13 supplied via the motive media connection 15. To prevent accumulation of reactant or product components inert under the conditions of methanol synthesis in the synthesis loop a stream is diverted from a portion of the residual gas stream RG 19 as purge gas stream 20 and supplied to a further use.

The raw methanol stream 21 is supplied to a further workup to obtain pure methanol (not shown).

In the case of the example according to FIG. 1 the recirculation rate R=4.6.

Figure 2:
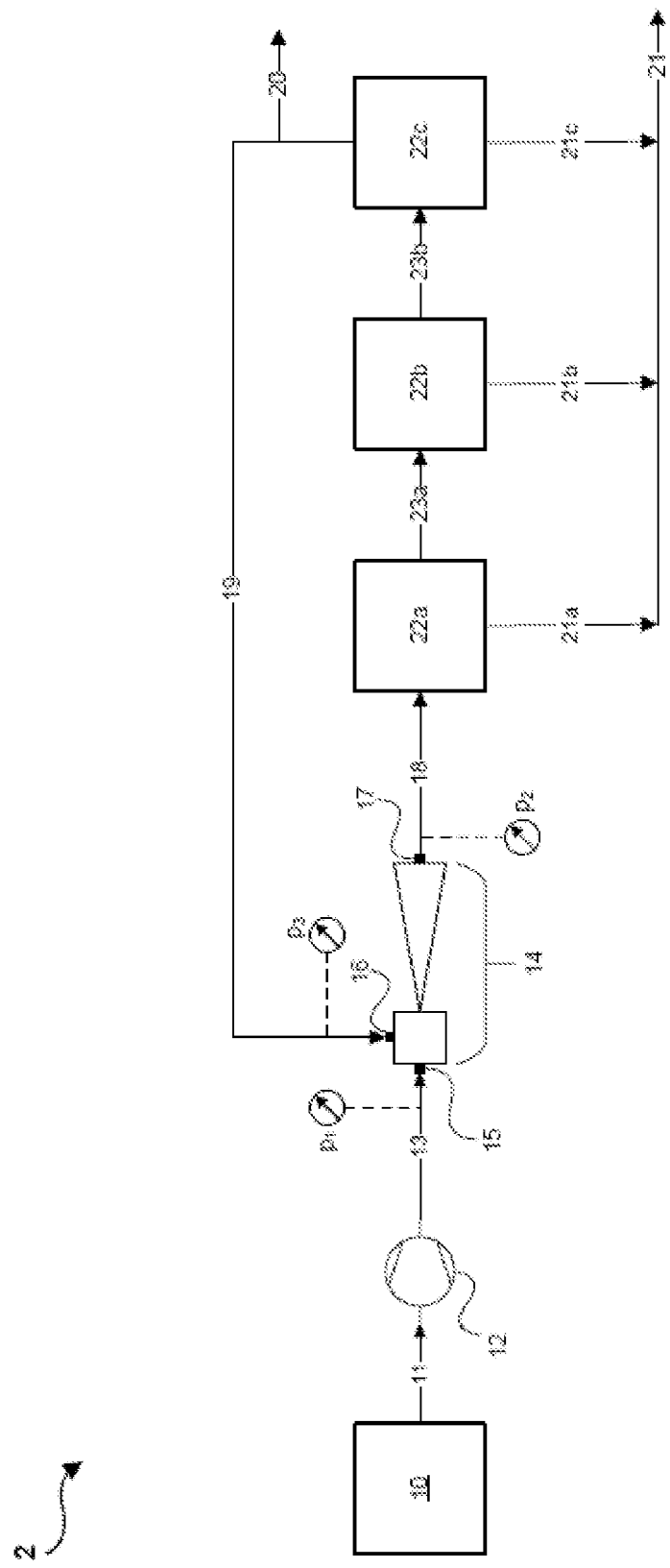
FIG. 2 shows a block flow diagram of an inventive process or an inventive plant according to a second example of the invention, wherein the process comprises three synthesis stages.

FIG. 2 shows a highly simplified block flow diagram of an inventive process (or an inventive plant) 2 according to a second example of the invention. The process according to FIG. 2 comprises three synthesis stages (or reactor stages) 22a, 22b and 22c.

The example according to FIG. 2 differs from the example according to FIG. 1 in that instead of a single synthesis stage 22 the process instead comprises three serially arranged synthesis stages 22a, 22b and 22c. Furthermore, the make-up gas stream 11 from the compressor 12 is only compressed to 90 bar relative to the pressure of the compressed make-up gas stream MG 13. Due to the presence of three serially arranged synthesis stages and the resulting higher carbon conversion (conversion of carbon bound in the synthesis gas to carbon bound in methanol) the "per pass" recirculation rate R is only 1.0.

Each of the synthesis stages 22a, 22b and 22c comprises means for cooling, condensing and separating raw methanol. This is accordingly discharged from the corresponding synthesis stages 22a, 22b und 22c as three separate raw methanol streams 21a, 21b and 21c. The three raw methanol substreams 21a, 21b und 21c are subsequently combined to afford an overall raw methanol stream 21. The raw methanol stream 21 is supplied to a further workup to obtain pure methanol (not shown). A stream of unconverted synthesis gas is also separated from the respective raw methanol stream per synthesis stage. In the case of the first synthesis stage 22a the unconverted synthesis gas is supplied to the second synthesis stage 22b as intermediate gas stream 1G 23a. The synthesis gas not converted in the second synthesis stage 22b is supplied to the third and last synthesis stage 22c as intermediate gas stream IG 23b. Finally, synthesis gas not converted into methanol and water in the third synthesis stage 22c is recycled to the suction port 16 of the jet pump 14 as residual gas stream RG 19 and therein in turn combined with the make-up gas stream MG 13 supplied via the motive media connection 15.

Depending on the process mode it is also possible for substreams to be diverted from the respective intermediate gas streams IG 23a and/or 23b and recycled not into the subsequent synthesis stage but rather to the motive media connection 15 of the jet pump 14.

To prevent accumulation of reactant or product components inert under the conditions of methanol synthesis in the synthesis loop, in the case of the example according to FIG. 2 too, a purge gas stream 20 is diverted from the residual gas stream RG 19 and supplied to a further use.

In the case of the example according to FIG. 2 the recirculation rate R=1.0.

The following numerical examples serve to further elucidate the invention. The numerical examples were generated using Aspen Plus® simulation software. The examples assume a "worst-case scenario" namely the case of a synthesis gas comprising exclusively carbon dioxide as the carbon oxide which is very unfavourable for methanol formation. In such a case the required recirculation rate is particularly high since the thermodynamic equilibrium is markedly on the reactant side and the carbon conversion (conversion of carbon in the synthesis gas into methanol) is comparatively low.

The following table shows a comparison between two configurations, according to the prior art and the invention, for a process having a single synthesis stage. Comparative Example 1 corresponds to a configuration having a dedicated residual gas compressor while Example 1 corresponds to a configuration having a jet pump as shown in FIG. 1.

|  | Comparative Example 1 (residual gas compressor) | Example 1 (jet pump) |
|---|---|---|
| Pressure at compressor inlet (stream 11)/bar | 30 | 30 |
| Recirculation rate | 4.6 | 4.6 |
| Pressure drop over synthesis stage/bar | 2 | 2 |
| Pressure at compressor outlet (stream 13)/bar | 80 | 95 |
| Normalized power demand for compression work of compressor 12 | 100% | 120% |

The omission of the residual gas compressor according to Comparative Example 1 and replacement of this residual gas compressor by a jet pump according to Example 1 increases the power demand of the compressor 12 by 20%. Especially in the case of plants on a small or intermediate scale the associated higher operating costs can however be overcompensated by the simultaneously falling capital and maintenance costs.

The following table shows a comparison between two configurations, according to the prior art and the invention, for a process having three serially arranged synthesis stages. Comparative Example 2 corresponds to a configuration having a dedicated residual gas compressor while Example 2 corresponds to a configuration having a jet pump as shown in FIG. 2.

|  | Comparative Example 2 (residual gas compressor) | Example 2 (jet pump) |
|---|---|---|
| Pressure at compressor inlet (stream 11)/bar | 30 | 30 |
| Recirculation rate | 1.0 | 1.0 |
| Pressure drop over synthesis stage/bar | 6 | 6 |
| Pressure at compressor outlet (stream 13)/bar | 80 | 90 |
| Normalized power demand for compression work of compressor 12 | 100% | 112% |

Since Comparative Example 2 and Example 2 relate to a three-stage synthesis with intermediate condensation of the raw methanol the carbon conversion "per pass" is higher and the recirculation rate is correspondingly several times lower than according to Comparative Example 1 and Example 1. The pressure drop over the synthesis stages is 6 bar instead of 2 bar due to the presence of three times as many synthesis stages.

The omission of the residual gas compressor according to Comparative Example 2 and replacement of this residual gas compressor by a jet pump according to Example 2 increases the power demand of the compressor 12 by only 12%. This is a surprising finding in view of the fact that the pressure drop in the case of the multistage synthesis according to FIG. 2 is 3 times as high as the single-stage synthesis according to FIG. 1 and must be compensated by compression. In this case the low recirculation rate of 1.0 thus has an overcompensating effect in terms of the required compressor power demand despite the higher pressure drop in the synthesis loop.

Synthesis gases having a high carbon monoxide content result, even in single-stage configurations, in a high "per pass" carbon conversion, as a result of which correspondingly lower recirculation rates are required. The abovementioned effect should therefore come into play especially also in the case of single-stage or two-stage processes having low recirculation rates which exhibit a low pressure drop over the synthesis stages.

LIST OF REFERENCE SYMBOLS 1, 2 Process, Plant
10 Apparatus for synthesis gas production
11 Make-up gas stream
12 Compressor
13 Compressed make-up gas stream MG
14 Jet pump
15 Motive media connection
16 Suction port
17 Pressure port
18 Synthesis gas stream SG
19 Residual gas stream RG
20 Purge gas stream
21, 21a, 21b, 21c Raw methanol stream
22, 22a, 22b, 22c Synthesis stage or reactor stage
23a, 23b Intermediate gas stream IG
$p_1$, $p_2$, $p_3$ Measurement and control sites for pressure It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A process for producing methanol, comprising:
   a) providing and compressing a make-up gas stream, wherein the make-up gas stream comprises at least one carbon oxide and hydrogen;
   b) reacting a synthesis gas stream in a synthesis stage over a solid methanol synthesis catalyst, wherein raw methanol and a residual gas stream are obtained and wherein the raw methanol after cooling and condensation as liquid reaction product and the residual gas stream are discharged from the synthesis stage;
   c) combining the residual gas stream with the make-up gas stream to obtain the synthesis gas stream,
wherein the residual gas stream and the make-up gas stream are combined using a jet pump, wherein the compressed make-up gas stream is supplied to the jet pump as motive medium via its motive media connection at a pressure $p_1$ and the residual gas stream is supplied to the jet pump as suction medium via its suction port at a pressure $p_3$ and wherein the synthesis gas stream is discharged from the jet pump via its pressure port at a pressure $p_2$ and subsequently supplied to the synthesis stage and wherein $p_1 > p_2 > p_3$.

2. The process according to claim 1, wherein for a recirculation rate R defined as $$R = \frac{\text{Volume flow}(RG)}{\text{Volume flow}(MG)},$$

$0.3 \leq R \leq 2.0$.

3. The process according to claim 1, wherein the process comprises a plurality N of serially arranged synthesis stages, wherein the raw methanol after cooling and condensation as liquid reaction product is discharged from each of the synthesis stages and the residual gas stream is discharged from the last of the N synthesis stages.

4. The process according to claim 3, wherein $N \geq 2$.

5. The process according to claim 1, wherein the proportion of carbon dioxide in the carbon oxides in the make-up gas stream MG is at least 50% by volume.

* * * * *